(12) United States Patent
McKay

(10) Patent No.: US 7,318,840 B2
(45) Date of Patent: Jan. 15, 2008

(54) INTERVERTEBRAL DISC TREATMENT DEVICES AND METHODS

(75) Inventor: William F. McKay, Memphis, TN (US)

(73) Assignee: SDGI Holdings, Inc., Wilmington, DE (US)

( * ) Notice: Subject to any disclaimer, the term of this patent is extended or adjusted under 35 U.S.C. 154(b) by 0 days.

(21) Appl. No.: 10/990,823

(22) Filed: Nov. 17, 2004

(65) Prior Publication Data

US 2006/0004456 A1    Jan. 5, 2006

Related U.S. Application Data

(63) Continuation of application No. 10/165,347, filed as application No. PCT/US00/42610 on Dec. 6, 2000, now abandoned.

(60) Provisional application No. 60/169,148, filed on Dec. 6, 1999.

(51) Int. Cl.
*A61F 2/44* (2006.01)

(52) U.S. Cl. .................. 623/17.11; 623/17.16

(58) Field of Classification Search ............ 623/17.11, 623/17.12, 17.13, 17.14, 17.15, 17.16; 606/61
See application file for complete search history.

(56) References Cited

U.S. PATENT DOCUMENTS

| | | | |
|---|---|---|---|
| 4,904,260 A | 2/1990 | Ray et al. | |
| 5,514,180 A * | 5/1996 | Heggeness et al. | 623/17.16 |
| 5,645,597 A * | 7/1997 | Krapiva | 606/61 |
| 5,916,870 A | 6/1999 | Lee et al. | |
| 5,948,428 A | 9/1999 | Lee et al. | |
| 5,964,807 A * | 10/1999 | Gan et al. | 424/423 |
| 5,994,325 A | 11/1999 | Roufa et al. | |
| 6,224,630 B1 * | 5/2001 | Bao et al. | 623/17.16 |
| 6,419,704 B1 * | 7/2002 | Ferree | 623/17.12 |
| 2001/0006948 A1 | 7/2001 | Kang et al. | |
| 2001/0016195 A1 | 8/2001 | Tobinick | |
| 2001/0024823 A1 | 9/2001 | Vukicevic et al. | |
| 2001/0027199 A1 | 10/2001 | Olmarker et al. | |
| 2001/0055594 A1 | 12/2001 | Olmarker et al. | |

FOREIGN PATENT DOCUMENTS

| | | |
|---|---|---|
| WO | WO 97/22371 | 6/1997 |
| WO | WO 99/43271 | 9/1999 |
| WO | WO 00/62832 | 10/2000 |
| WO | WO 00/75659 | 12/2000 |
| WO | WO 01/76654 | 10/2001 |
| WO | WO 02/00142 | 1/2002 |

* cited by examiner

*Primary Examiner*—Cris Rodriguez
*Assistant Examiner*—Candice C. Stokes
(74) *Attorney, Agent, or Firm*—Woodard, Emhardt, Moriarty, McNett & Henry LLP

(57) ABSTRACT

Intervertebral disc treatment devices and methods are provided. An intervertebral disc treatment device includes a fibrous body sized for introduction into a disc cavity of a damaged disc wherein the body incorporates an effective amount of a tissue growth factor. Intervertebral disc treatment apparatuses are also described that include such a disc treatment device in combination with a delivery apparatus for retaining and selectively releasing the device into the disc cavity. Methods for treatment include providing a disc treatment device as described above and inserting the device into an opening in an annulus fibrous and into the disc cavity. The methods further include stimulating tissue growth within the disc cavity of the intervertebral disc.

50 Claims, 7 Drawing Sheets

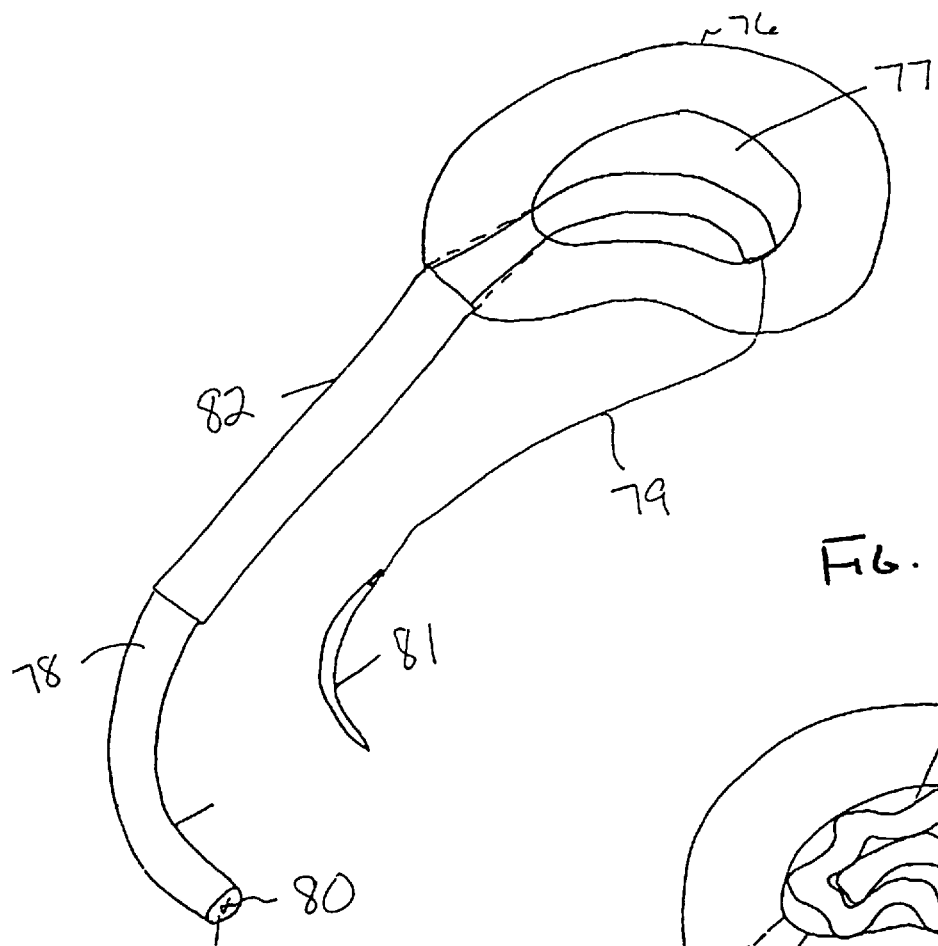

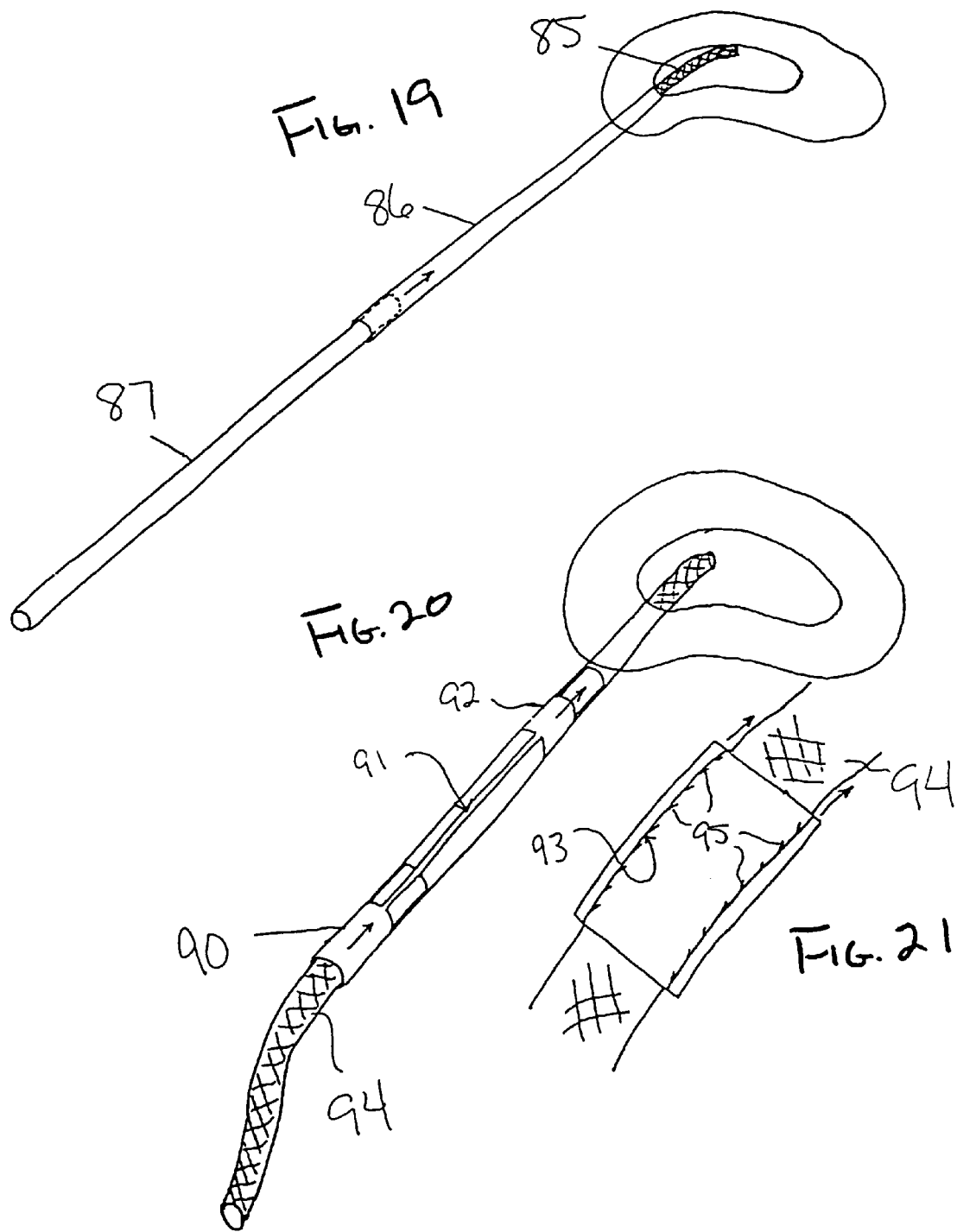

INTERVERTEBRAL DISC TREATMENT DEVICES AND METHODS

REMARKS TO RELATED APPLICATIONS

This application is a continuation of U.S. patent application Ser. No. 10/165,347, filed Jun. 6, 2002 now abandoned, which is the National Stage of International Patent Application No. PCT/US00/42610 filed Dec. 6, 2000 designating the United States and published in English, which claims the benefit of U.S. Provisional Patent Application No. 60/169,148 filed Dec. 6, 1999, each of which is hereby incorporated by reference in its entirety.

BACKGROUND OF THE INVENTION

The present invention relates generally to devices and methods for restoring function to the spine. Specifically, the invention relates, to devices and methods for treating a damaged intervertebral disc while retaining the annulus fibrosis of the disc and, advantageously, stimulating tissue formation to restore function Go the original disc structure.

Back pain affects millions of people and is a common cause of disability for the middle-aged working population. A frequent cause of back pain is rupture or deceleration of intervertebral discs. Intervertebral discs, located between the endplates of adjacent vertebrae, stabilize the spine, distribute forces between vertebrae, and cushion vertebral bodies. An intervertebral disc includes the annulus fibrosus, a structure that surrounds and confines an inner component, the nucleus pulposus. The annulus fibrosis is composed of a ring of collagen fibers and fibrocartilage embedded in a generally amorphous base substance. The nucleus pulposus is comprised of a mucoid material containing mainly glycoproteins and some collagen. In a healthy, undamaged spine, the annulus fibrosus prevents the nucleus pulposus from protruding outside the disc space and also resists torsional and bending forces applied to the disc.

Intervertebral discs may be displaced or damaged due to disease or aging. Disruption of the annulus fibrosus can allow the nucleus pulposus to protrude into the vertebral canal or intervertebral foramen, a condition known as a herniated or slipped disc. A rupture in the annulus fibrosis can allow the escape of nucleus pulposus components. The extruded nucleus pulposus may press on a spinal nerve, which may result in nerve damage, pain, numbness, muscle weakness and paralysis. Furthermore, as a disc dehydrates and hardens due to age or disease, the disc space height will be reduced, leading to instability of the spine, decreased mobility and pain. Moreover, excessive movement of the spinal segments caused by the disc space height reduction could weaken the annulus fibrosus and, in certain cases, tear it.

Common methods of providing relief for damaged intervertebral discs include surgical removal of all or a portion of the intervertebral disc, followed by fusion of the adjacent vertebrae. Although fusion can eliminate the above symptoms, the restricted motion of the fused segment increases the range of motion required of the adjoining intervertebral discs and could enhance their degeneration.

Attempts at overcoming the problems with fusion include replacing the entire intervertebral disc with a mechanical, articulating intervertebral disc spacer. Many of these devices utilize multicomponent polymeric and metallic materials in an attempt to simulate the normal, healthy intervertebral disc motion. Such materials may disintegrate in the body and break down under repeated stressing over prolonged periods. Other attempts at overcoming the problems with replacing the entire intervertebral disc have included replacing the nucleus pulposus with elastomeric materials such as hydrogels.

SUMMARY OF THE INVENTION

The present invention relates to methods and devices for repairing an intervertebral disc which include promoting synthesis of tissue components, such as nucleus pulposus and/or annulus fibrosus components, of the disc. In one aspect, the present invention provides a device which can be used to promote the synthesis of disc components in vivo to treat intervertebral discs. In particular, provided is a device for treating an intervertebral disc of a vertebrate, while retaining an intact annulus fibrosis, the device including a compressible fibrous body configurable to a compressed state for passage through an opening in the annulus fibrosis and into a disc cavity defined by the annulus fibrosis. The body is also configurable to an expanded state to reside within the disc cavity and have a dimension greater than the opening so as to resist expulsion from the opening. The body in incorporates an effective amount of an active agent, such as a tissue growth factor, or cells (e.g. stem, nucleus pulposus, annulus fibrosis, or fibroblast cells), such cells optionally genetically modified to express effective amounts of a tissue growth factor, to stimulate tissue growth in the disc structure.

Another aspect of the invention provides an intervertebral disc treatment device including a fibrous body sized for passage through an opening in the annulus fibrosis and into a disc cavity defined by the annulus fibrosis. The body is formed of fibers having coated thereon a solid carrier matrix incorporating a substance for promoting tissue growth.

In the above-discussed aspects of the invention, the body of the device may be partially or completely bioresorbable. In addition, the body may be sized and configured to provide temporary or permanent prosthetic function, by being dimensioned to participate in the distribution of compressive loads between adjacent vertebral bodies. For example, the body may be adapted to physically maintain a space in the disc as new tissue is generated, and provide a substrate nor tissue ingrowth which locks the implant in place and reinforces regenerated tissues to help maintain disc space height. In another inventive aspect, be body may be non-prosthetic, while delivering a substance for promoting tissue growth in the disc structure. In such non-prosthetic applications, the device can be dimensioned, or can be formed of a material having compressive properties, such that it does not participate in the distribution of loads between the adjacent vertebral bodies. Nonetheless, such a non-prosthetic body may deliver the tissue growth substance so as to enhance the function or integrity of the disc structure.

Another feature of the invention provides an intervertebral disc repair apparatus that has a disc treatment device as described above in combination with a delivery apparatus. The delivery apparatus is adapted to retain and selectively release the treatment device into the disc cavity, and may for example include a member having a proximal end, a distal end and a lumen extending longitudinally therethrough. The disc repair device is disposed within the lumen of the apparatus. The delivery apparatus is adapted to translate the disc repair device distally through the lumen, through an opening in the annulus fibrosis, and into the disc cavity.

Yet other features of the invention include methods for treating an intervertebral disc, which involve introducing a disc treatment device as described above into the disc cavity of a damaged disc.

In additional embodiments of the invention, methods for treating a disc having an annulus fibrosis having an opening therein, which methods include as providing a body configured for passage through the opening and for blocking effluence from the opening once positioned within the disc cavity. The body is passed through the opening and into the disc cavity, so as to block effluence from the opening. A tissue growth composition is also provided within the disc cavity, either as a component of the body or separately.

It is an object of the invention to provide devices and methods that may be used to provide therapy to a damaged disc by promoting in vivo synthesis of components within the disc structure.

It is a further object of the invention to provide methods and devices for preventing effluence from a damaged intervertebral disc.

These and other objects and advantages of the present invention will be apparent from the descriptions herein.

BRIEF DESCRIPTION OF THE FIGURES

FIGS. 16-18 illustrate elongate implants of the invention and apparatuses and methods for their introduction into the disc cavity.

FIGS. 19-21 illustrate elongate implants of the invention and additional apparatuses and methods for their introduction into the disc cavity.

DESCRIPTION OF THE PREFERRED EMBODIMENTS

For the purposes of promoting an understanding of the principles of the invention, reference will now be made to preferred embodiments thereof and specific language will be used to describe the same. It will nevertheless be understood that no limitation of the scope of the invention is thereby intended, such alterations and further modifications of the invention, and such further applications of the principles of the invention as illustrated herein, being contemplated as would normally occur to one skilled in the art to which the invention relates.

The present invention provides intervertebral disc treatment devices, apparatuses and methods. Preferred devices include a fibrous body configurable to smaller (compressed) and larger (relaxed) dimensional states. In the small configuration the body is adapted for passage through an opening in the annulus fibrosis and into a disc cavity defined by the annulus fibrosis. In the larger configuration the body is dimensioned sufficiently to resist expulsion from the annulus opening when positioned within the disc cavity. The body incorporates an effective amount of a substance which promotes tissue formation in the disc structure. Inventive apparatuses are provided which include such fibrous bodies in combination with a delivery apparatus adapted to retain and selectively release the bodies into the disc cavities, and inventive methods are also provided can be performed using the devices and apparatuses of the invention.

Figure 1:
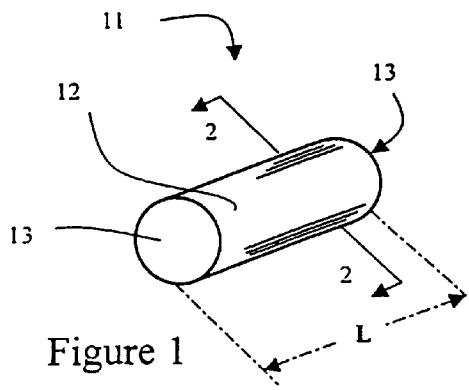
FIG. 1 is a perspective view of a disc treatment device of the present invention.

Referring now to FIG. 1, a preferred intervertebral disc treatment device 11 is illustrated that includes an outer surface 12, and opposing ends 13. Device 11 is elongate in shape, having a generally cylindrical configuration with a circular cross-section. Device 11 has a length L and a cross-sectional dimension adapted for insertion into the disc cavity of a damaged disk. In preferred devices, length L, will be about equal to or less than a horizontal cross-sectional dimension of the disc cavity of a human disc (e.g. the anterior-posterior width and/or the lateral width of the disc cavity), typically in the range of about 1.5 cm to about 3.5 cm. Preferably also, device 11 will be of a size and composition so as to avoid the exertion of substantial lateral pressure upon the annulus fibrosis by the device, which may cause or facilitate the development of a rupture in the annulus fibrosis. Device 11 will have or be compressible radially to have a greatest cross-sectional dimension which renders device 11 suited for insertion into an opening in a disc annulus, such greatest cross-sectional dimension typically being in the range of about 0.3 cm to about 2.0 cm. Device 11 may, for instance, have a body comprised of a woven or nonwoven fibrous material, including but not limited to a fibrous mesh. The body of device 11 is also preferably swellable in the presence of aqueous fluids, for example swelling upon absorbing aqueous fluids into pores created between fibers in a fibrous body, and/or upon hydration of the fibers themselves.

Figure 2:
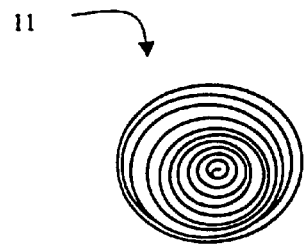
FIG. 2 is an enlarged, cross-sectional view of the device of FIG. 1 taken along a vertical plane through line 2-2 and viewed in the direction of the arrows.

Referring now to FIG. 2, shown is an enlarged, cross-sectional view taken in a vertical plane along line 2-2 of FIG. 1 and viewed in the direction of the arrows. As illustrated, device 11 may be formed as a roll of a sheet material, for instance a fibrous mesh, to provide multi-layered device. Using such a multi-layered configuration, the device may be constructed to prevent, or alternatively to allow, for unrolling or unfolding of the layers after insertion into the disc cavity. For instance, layers may be permanently affixed to one another such as by bonding, crosslinking or stitching, to prevent unfolding. On the other hand, layers may be free of permanent affixation to one another (e.g. non-affixed or only temporarily affixed), to allow the layers to unfold within the disc cavity. Such unfolding may, for example, participate in configuring the device to resist expulsion From an annulus fibrosis opening, and/or to occupy a modified volume within the disc cavity for supporting tissue ingrowth.

Figure 3:
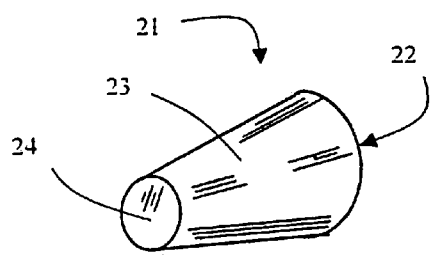
FIG. 3 is a perspective view of a further disc treatment device of the present invention having an annular ring shape.
Figure 4:
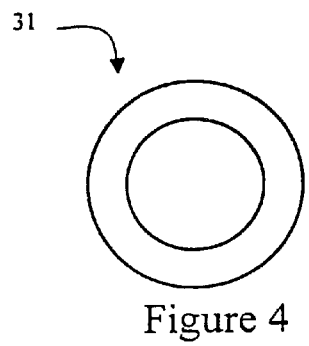
FIG. 4 is a perspective view of a further disc treatment device of the present invention.

Although a generally cylindrical disc repair device is shown in FIGS. 1 and 2, the device may assume a variety of other configurations including spherical, rectangular, conical, ring, and other shapes. It is preferred that the device be shaped so that it can facilitate blocking an opening in the annulus fibrosus of a damaged intervertebral, disc when positioned in the disc cavity. For example, the device may have a first end having a cross-sectional dimension smaller than another cross-sectional dimension along the device, for example having an increasing cross-sectional dimension along the device length such as occurs in a generally conical device. Referring now to FIG. 3, such a disc repair device 21 is shown, having a generally conical shape with a larger end 22 and an outer surface 23 that tapers towards a smaller opposing end 24. As another example, the device may be collapsible in upon itself to have a smaller overall cross-sectional dimension in a direction in which it is to be inserted, for example in the case of an annular ring. Shown in FIG. 4 is such a disc treatment device 31, having the shape of an annular ring. Device 31 preferably has an outer diameter, when expanded, approximating the horizontal width of the disc cavity, and can be collapsed upon itself to adopt a smaller overall cross-sectional dimension or insertion through an opening in the annulus fibrosis.

Figure 5:
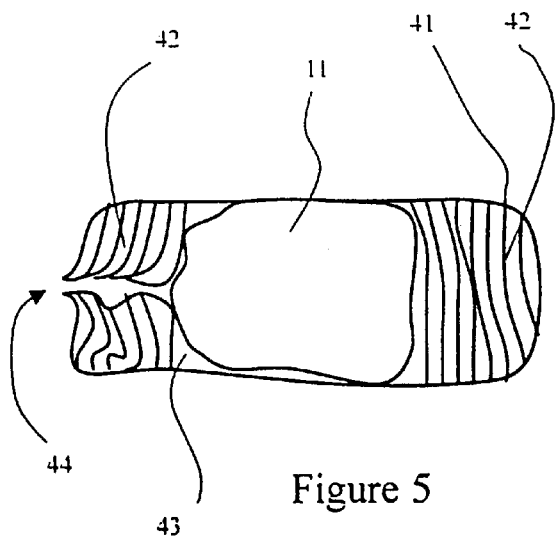
FIG. 5 is a side cross-sectional view illustrating the disc repair device shown in FIG. 1 positioned within an intervertebral disc.

With reference now to FIG. 5, shown is a side cross-sectional view of a intervertebral disc having positioned therein disc treatment device 11 of FIG. 1. As illustrated, an intervertebral disc 41 includes the annulus fibrosus 42 formed from multiple layers of type II collagenous tissue, bounding an internal disc cavity 43. Disc treatment device 11 is sized and configured to be contained within the disc cavity and in the illustrated embodiment has a vertical dimension to contact the upper and lower surfaces of the disc cavity formed by end plates of adjacent vertebrae. In addition, device 11 has a horizontal dimension substantially spanning the horizontal width of the disc cavity 43. Device 11 also abuts the inner surface of the annulus fibrosus 42 so as to facilitate blockage of effluence from disc cavity 43 via opening 44 in annulus fibrosus 42. Opening 44 in annulus fibrosis 42 often occurs posterolaterally, where the annulus fibrosis is no longer supported by the posterior longitudinal ligament. Thus, in most cases, device 11 or other disc treatment devices of the invention can be inserted via a posterolateral approach, although other approaches may be used which correspond to the location of the rupture in the disc to be treated, or which involve insertion of the device through a conservative, alternate opening created in a spaced location from the rupture.

Figure 6:
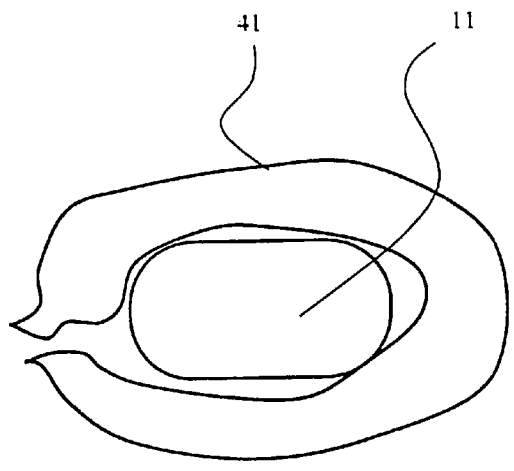
FIG. 6 is a superior view of the disc treatment device of FIG. 1 positioned in the disc cavity of an intervertebral disc.
Figure 7:
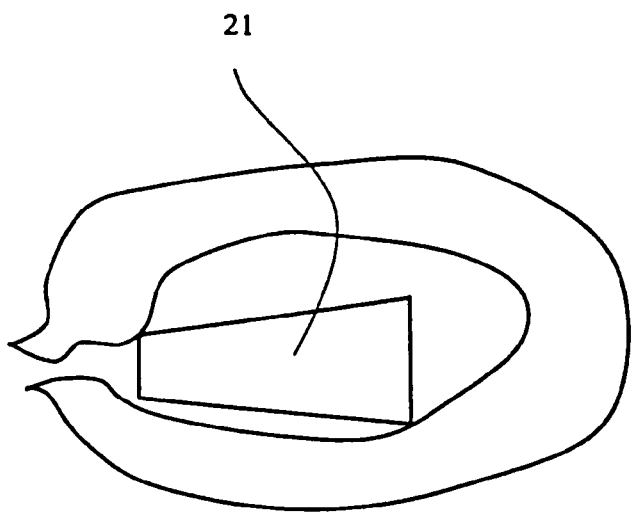
FIG. 7 is a superior view of the disc treatment device of FIG. 3 positioned in the disc cavity of an intervertebral disc.
Figure 8:
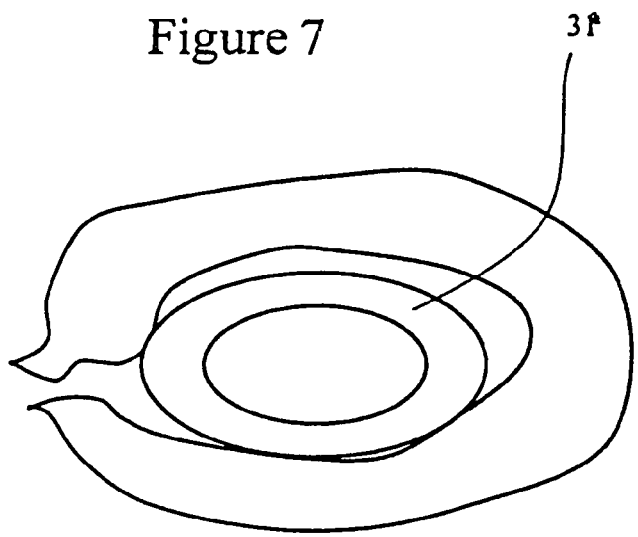
FIG. 8 is a superior view of the disc treatment device of FIG. 4 positioned in the disc cavity of an intervertebral disc.
Figure 9:
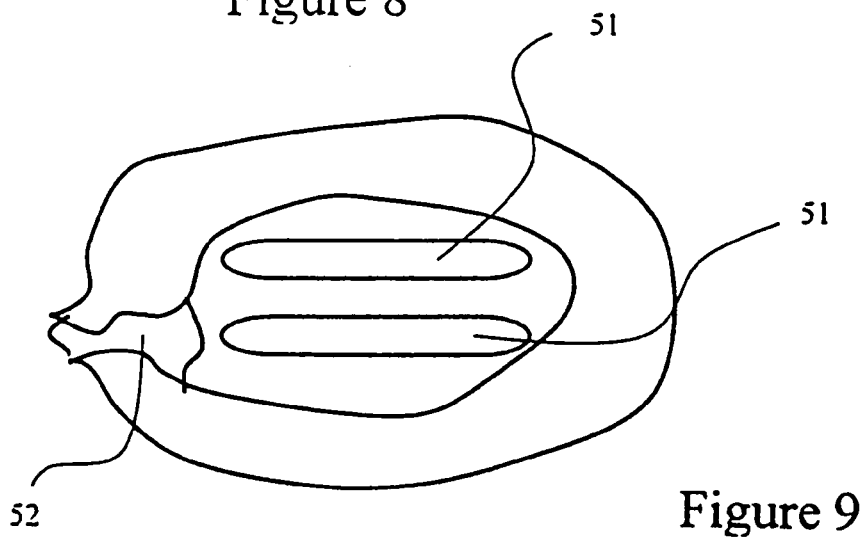
FIG. 9 is a superior view illustrating two disc treatment devices positioned in the disc cavity of an intervertebral disc, and wherein an opening in the annulus fibrosis is sealed with a sealant composition.
Figure 10:
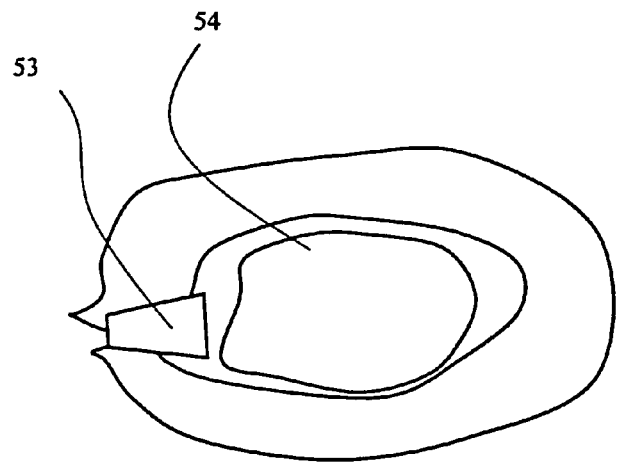
FIG. 10 is a superior view illustrating first and second disc treatment devices positioned within the disc cavity of an intervertebral disc, wherein one functions to seal a rupture in the annulus fibrosis.

With reference now to FIGS. 6, 7, and 8, shown are superior views of disc treatment devices 11, 21, and 31, respectively, positioned within the disc cavity of a ruptured disc.

The disc treatment devices of the invention may be formed from a wide variety of natural and/or synthetic materials, preferably natural and/or synthetic polymers. Natural polymers include, for example, collagen, elastin, and cellulose and may be obtained from natural sources by methods known to the skilled artisan, synthesized by methods known to those skilled in the art, or may be obtained commercially. Synthetic polymers which may be used in the present invention include, for example, polyamides, polyesters (e.g., Dacron), polyethylene, polyacrylonitrile, polyurethanes, polypropylenes or mixtures thereof. Combinations of natural and synthetic materials may also form an appropriate fibrous body for use in the present invention.

The preferred devices of the invention advantageously incorporate a tissue growth factor. In one embodiment the device includes a liquid or solid carrier containing the tissue growth factor. For example, a solid or liquid carrier containing the growth factor may be used to coat the exterior of the device, and/or may be incorporated within interstitial spaces (e.g. pores) occurring internally of the device. In addition, or alternatively, a solid carrier matrix containing the growth factor may be used to coat individual fibers from which the body of the disc treatment device is formed. The growth factor is generally suited to promote the formation of tissues, especially of the type(s) naturally occurring as internal or external components of the disc. For instance, the growth factor may promote the growth or viability of tissue or cell types occurring in the nucleus pulposus such as nucleus pulposus cells and chondrocytes, as well as space filling cells such as fibroblasts and connective tissue cells such as ligament and tendon cells. Alternatively or in addition, the growth factor may promote the growth or viability of tissue types occurring in the annulus fibrosus, as well as space filling cells such as fibroblasts and connective tissue cells such as ligament and tendon cells. Such growth factors include Transforming Growth Factor-beta (TGF-B) and members of the TGF-B superfamily, Fibroblast Growth Factor (FGF) and members of the FGF family, Platelet Derived Growth Factor (PDGF) and members of the PDGF family, members of the hedgehog family of proteins, interleukins, Insulin-like Growth Factor, (IGF) and members of the IGF family, colony stimulating factor (CSF) and members of the CSF family, Growth Differentiation Factors (GDFs), Cartilage Derived Growth Factors (CDGFs), Cartilage Derived Morphogenic Proteins (CDMPs), Bone Morphogenetic Proteins (BMPs), and mixtures thereof. BMPs are preferred.

A wide variety of BMPs have been identified and may be used in the present invention. Human BMPs, especially recombinant human BMPs, are preferred, including for instance BMPs 1, 2, 3, 4, 5, 6, 7, 8, 9, 10, 11, 12, 13, 14, 15, 16, 17 and 18. A variety of such BMPs have proven effective for forming soft connective tissues such as cartilage (e.g. BMP-2 and BMP-4) or ligament and tendon (e.g. BMP-12 and BMP-13), and these and other similarly functional proteins are used with preference in the instant invention. BMPs are available from Genetics Institute, Inc., Cambridge, Mass. and may also be prepared by one skilled in the art as described in U.S. Pat. No. 5,187,076 to Wozney et al.; U.S. Pat. No. 5,366,875 to Wozney et al.; U.S. Pat. No. 4,877,864 to Wang et a; U.S. Pat. No. 5,108,932 to Wang et al.; U.S. Pat. No. 5,116,738 to Wang et al.; U.S. Pat. No. 5,013,649 to Wang et al.; U.S. Pat. No. 5,106,748 to Wozney et al; and PCT Patent Nos. WO93/00432 to Wozney et al.; WO94/2693 to Celeste et al.; and WO94/26892 to Celeste et al. All BMPs are contemplated whether obtained as above or isolated from bone. Methods for isolating BMP from bone are described in U.S. Pat. No. 4,294,753 to Urist and in Urist et al., PNAS 371, 1984. Most preferably, the BMP or other growth factor will be non-osteoinductive or at the least insufficiently osteoinductive, to cause, a bony fusion of the vertebrae above and below the disc under treatment.

In one aspect of the invention BMP-12 and/or BMP-13 will be employed in an effective amount to stimulate growth of ligament and/or tendon connective tissue within the disc cavity, for instance as may be evidenced by increased synthesis of proteoglycans and collagens. Recombinant human BMP-13 is most preferred in this regard.

A wide variety of materials may be utilized as solid carriers. Examples include natural polymers such as collage, gelatin, elastin, cellulose, and the like.

In one preferred embodiment, the carrier is collagen. A wide variety of types of collagen may be used, including type I (found primarily in skin, tendon and bone), type II (found in cartilage), type III (found primarily in skin), fibrillar and non-fibrillar collagen. The collagen may be isolated from skin, bone, tendon, or cartilage by methods known to the skilled artisan and may be purified by methods known in the art. Alternately, the collagen may be purchased commercially. Moreover, atelopeotidic or telopeptidic collagen may be used.

In methods for disc treatment, the tissue growth factor may be applied to the device as described above or may be introduced into the disc space or cavity separately (e.g. by injection), or by recombinant DNA methods. For example, a nucleic acid sequence, such as a deoxyribonucleic acid sequence, encoding the particular growth factor, or an active fragment thereof, may be introduced into an appropriate vector The vector may be a wide variety of vectors typically used in gene transfer protocols, including, for example, retroviral vectors or adenovirus vectors. The vector construct may be synthesized by methods known to the skilled artisan. The nucleic acid sequence may be under the control of, and operably linked to, a promoter or other regulatory sequence known in the art. The promoter is preferably one which may be activated in the target cell by regulatory elements present in the target cell.

In one form of the invention, the disc repair device advantageously includes a therapeutically effective amount of the tissue growth factor. What constitutes an effective amount will vary depending on factors known to the skilled artisan, such as the specific growth factor used and the extent and type of the damage to the intervertebral disc. However, the disc repair device will typically contain about 2 mg to about 20 mg of the growth factor. When BMP-9 is used, for example, amounts applied may include about 8 mg to about 12 mg.

Figure 11:
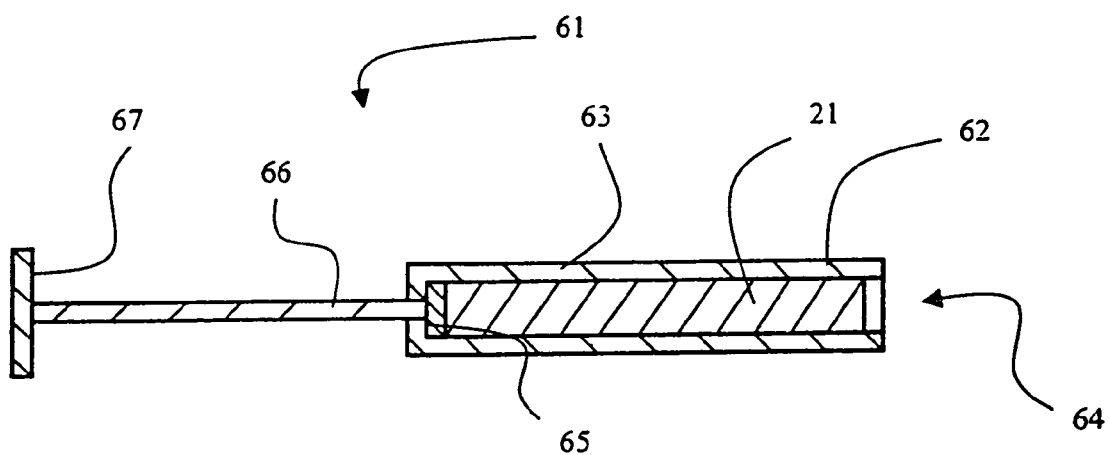
FIG. 11 is a side cross-sectional view of a disc treatment apparatus, showing the disc treatment device of FIG. 3 in a compressed conformation in the lumen of a delivery apparatus.

In another aspect of the invention, an intervertebral disc treatment apparatus is provided that includes a disc repair device as described above in combination with a delivery apparatus. Referring now to FIG. 11, apparatus 61 is shown that includes the generally conical disc repair device 21 of FIG. 3, in compressed configuration within the apparatus. The disc treatment apparatus 61 includes tubular or barrel member 62 having proximal end, a distal end, and a lumen 63 extending longitudinally therethrough. Member 62 may be similar to the barrel of a syringe as known in the art. Lumen 63 is configured for housing the disc repair device. Member 62 may be constructed or a wide variety of materials, including polytetrafluoroethylene (Teflon), polyethylene, polyurethane, nylon, glass, or combinations thereof.

Figure 12:
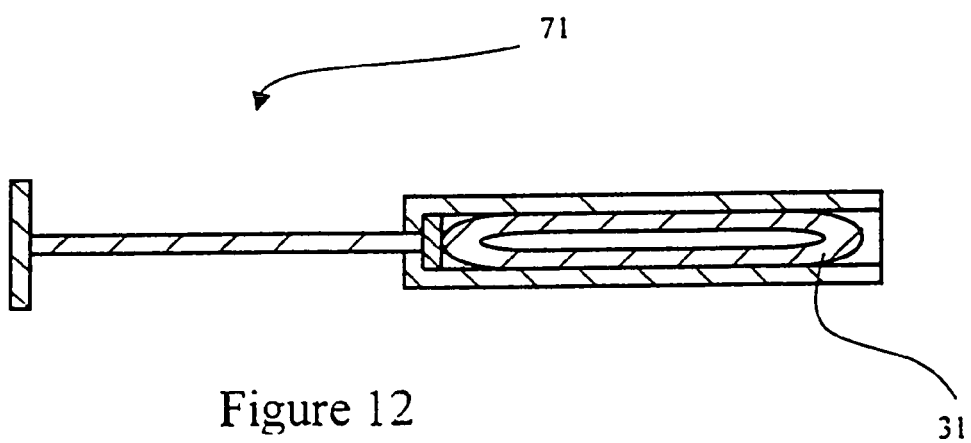
FIG. 12 is a side cross-sectional view of a disc treatment apparatus, showing the disc treatment device of FIG. 4 in a compressed conformation in the lumen of a delivery apparatus.

Disc repair delivery apparatus 61 further includes a translation member 64 at the proximal end of tubular member 62 or forcing the disc repair device 21 distally through lumen 63, through an opening in the annulus fibrosus of a damaged disc, and into the disc cavity of the disc. Translation member 64 may be an elongated member sized to at least partially fit within lumen 63 of member 62 and which is capable of pushing the disc repair device distally along lumen 63. For example, member 64 may be a plunger including a handle 67, an elongate rod 66, and an internal member 65 substantially spanning the lumen 63 of tubular member 62, as seen in FIG. 8. Alternately, translation member 64 may be replaced by other means for translating device 21 along lumen 63. For example fluid (e.g. liquid) driven mechanisms may be used. The disc repair device, such as disc repair device 21, is preferably placed in a collapsed or compressed conformation as shown in FIG. 11, advantageously by manual force, prior to or upon positioning the device 21 in lumen 63 shown in FIG. 12 is a similar disc treatment apparatus 71 except including therein device 31 of FIG. 4 in compressed configuration, instead of device 21 of FIG. 3.

In another aspect of the invention, methods of treating an intervertebral disc are provided. In one embodiment, a method of treating an intervertebral disc includes providing a disc treatment device as described above, such as a fibrous body sized for introduction into an opening of an annulus fibrosus of a damaged intervertebral disc, and inserting the fibrous body into and through the opening, and blocking effluence from the opening.

Figure 13:
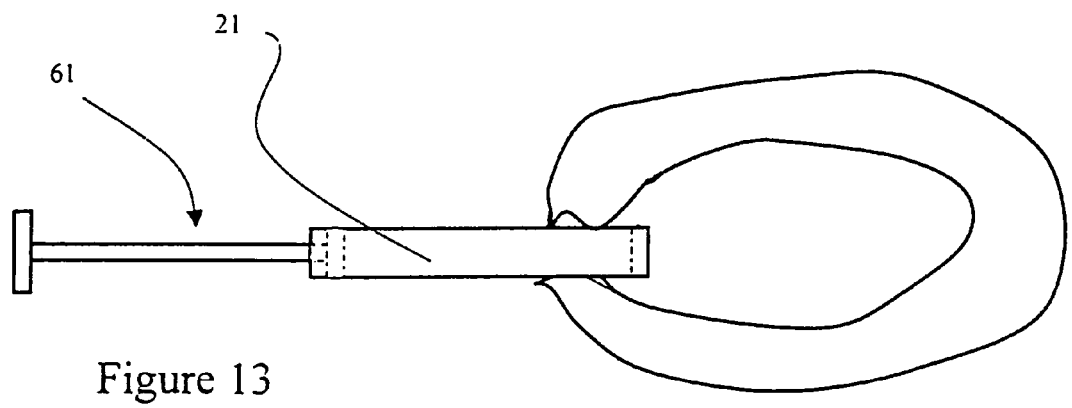
FIGS. 13 and 14 are superior views illustrating the use of the disc treatment apparatus of FIG. 11 to release the disc treatment device of FIG. 3 into a disc cavity.
Figure 14:
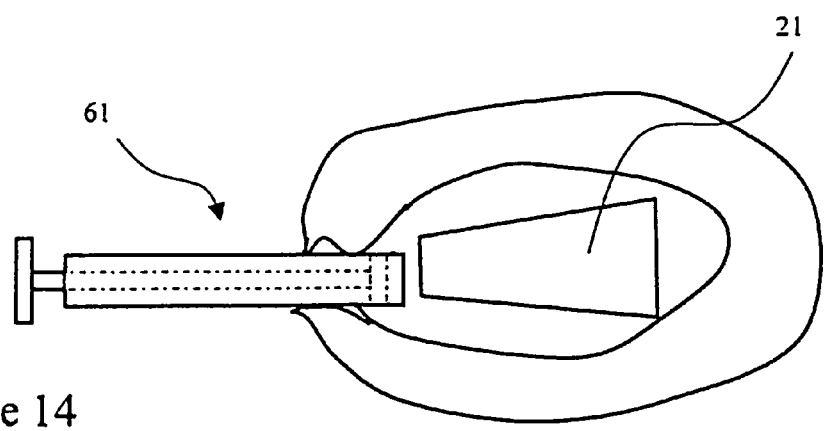

In order to place the disc repair device in the disc cavity, a disc repair delivery apparatus 61 or 71 as described above may be used. As seen in FIGS. 13 and 14, lumen 63 of tubular member 62 is aligned with the opening in the annulus fibrosus of an intervertebral disc so that the disc repair device may be pushed distally along lumen 63, through the opening in the annulus and into the disc cavity. The disc repair device will then adopt an expanded conformation as seen in FIG. 14.

Figure 15:
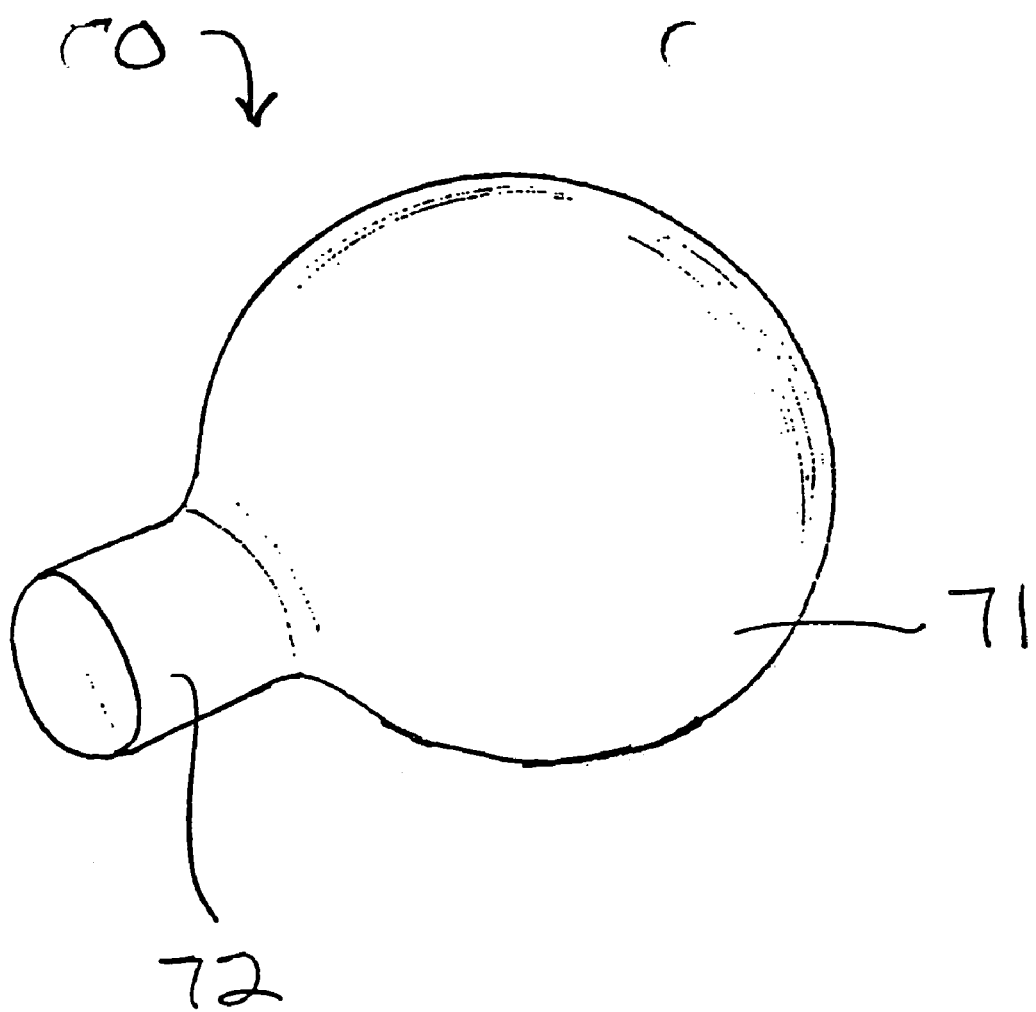
FIG. 15 is a perspective view of another disc treatment device of the invention.

Referring now to FIG. 15, shown is an alternative disc treatment device 70, having a generally bulbous end 71 and a generally cylindrical end 72. Bulbous end 71 has a greatest cross-sectional diameter greater than that of cylindrical end 72. In one mode of use, device 70 can be compressed and loaded into a cylindrical delivery apparatus, and delivered through a hole in the annulus and into the disc cavity, preferably first introducing bulbous end 71. Device 70 can then expand within the disc cavity.

With reference now to FIGS. 16-18, illustrated is one made of introducing an elongate implant body through an opening 75 in an annulus 76 (e.g. in the location or a rupture opening), and into the disc cavity 77. An elongate, cylindrical implant 78 is provided (e.g. a Dacron mesh cylinder) having an internal suture 79 or other similar structure running therethrough and tied off or otherwise connected a an end 80 of implant 78. The other end of suture 79 is tied to a curved needle 81. To deliver the implant 78, implant 78 can be loaded within a rigid tube 82, with needle 81 and an exposed length of suture 79 extending therefrom. Needle 81 can be passed through opening 75 in annulus 76 and into the disc cavity 77, and then back through the annulus 76 at a spaced location from opening 75, for example at an opposite, posterolateral position which can be surgically accessed separately. Suture 79 can then be pulled to in turn pull implant 78 into the disc cavity 77. Suture 79 can then be closely cut or broken so as to partially retract into the annulus.

FIG. 19 illustrates another apparatus and method for delivering an implant 85, such as a cylindrical Dacron mesh implant, into a disc cavity. Implant 85 is loaded within a rigid cannula tube 86, which in turn is passed through the opening in the annulus. In this regard, implant 85 can be loaded in a dry or wet state, preferably a dry, compressed state. Implant 85 is then advanced through the tube 86 using push or plunger rod 87, and into the disc cavity. After implantation, a dry implant 85 will hydrate, and preferably swell, in situ in the disc cavity. If desired, the internal surface of the tube 86 and the exterior surface of the rod 87 can be provided with respective cooperating members, such as threads, to assist in controllably advancing implant 85 through the tube 86. For example, the inner surface of tube 86 may bear threads, while the external surface of rod 87 bears corresponding threads. In this fashion, rotation of rod 87 in relation to tube 86 will advance rod 87 through tube 86, thereby pushing implant 85 through tube 86. In addition, or in the alternative, the implant 85 and/or the internal surface of tube 86 may be coated with a suitable, biocompatible lubricant to reduce the friction between the implant 85 and the tube 86 during the advancement operation.

Referring now to. FIGS. 20 and 21, shown is another apparatus and method for delivering an implant through an annulus opening and into the disc cavity. A rigid cannula tube 90 defines an opening such as a slot 91 in a sidewall thereof. A plurality of openings (e.g. opposed slots) may also be provided. A friction member 92 is mounted over tube 90 and includes an engaging portion 93 extending into slot 91 so as to provide frictional contact with an implant 94 inside tube 90. In this fashion, implant 94 can be advanced through tube 90 by corresponding advancement of the friction member 92 while its engaging portion 93 frictionally engages implant 94 through slot 91. In this regard, the frictional engagement of the implant 94 can optionally be facilitated by the presence of teeth 95 (e.g. directional as shown) or other roughened surface features such as grooves or proturbances on the engaging portion 93 of friction member 92, and/or by selection a materials exhibiting a coefficient of friction with the implant suitably high to effectively advance the implant through the tube 90. Further, the frictional engagement of engaging portion 93 with implant 94 may be releasable, for example by constructing a deflectable friction member 92 which in a relaxed state disengages engaging portion 93 from the implant, but in a compressed state (e.g. by manually squeezing) engages engaging portion 93 with the implant 94, or vice versa.

A tissue growth factor may be provided on the body of or within the device, separately within the disc space of the intervertebral disc, or both. When included separately in the disc space, the tissue growth factor may be provided within the disc space either before or after the disc repair device is positioned. Injection of an aqueous fluid containing the tissue growth factor into the disc repair device may also facilitate expansion of a hydratable, swellable disc repair device immediately after implantation. The disc repair device may be adapted and dimensional such that when in its expanded or swollen conformation, the device is of a sufficiently large dimension to contact the overlying and underlying endplates, preferably under compression, so as to secure the device in place in the disc cavity and desirably dissipate compressive loads from the spine.

All or a portion of the nucleus pulposus of a damaged intervertebral disc may be removed prior to inserting the device. Moreover, the method may also be followed for preventing escape of the nucleus pulposus from a damaged intervertebral disc, as the disc repair devices or the present invention may act as a plug.

It Will be understood that various ways of orienting a disc repair device of the present invention in disc cavity are contemplated in the invention. A single disc repair device can have its longitudinal axis positioned perpendicular to longitudinal axis of the vertebral column, or two or more devices can be positioned in this manner (e.g. two devices used in a bilateral configuration).

Disc treatment devices may be inserted through pre-existing (e.g. rupture) opening in the annulus fibrosus or they may be inserted through a cut or incised opening. In one preferred manner of carrying out the invention, the one or more devices provided to the disc cavity will substantially fill the existing void in the cavity, and may also have a sufficient vertical dimension to contact the upper and lower surfaces within the cavity, for instance so as to be effective to absorb compressive loads of the spine.

Delivery apparatuses in accordance with the invention may also be adapted for non- or minimally-invasive delivery of the intervertebral disc treatment device. For example, such an apparatus can include a cannulated device of sufficient length to extend to the disc cavity from an exterior operating position, and the disc, treatment device can be advanced (e.g. in compressed or collapsed form) through and out the distal end of the cannula and into the disc cavity. For example, such a procedure may immediately follow a known discectomy protocol, including for instance micro-discectomies, endoscopic discectomies, and laparoscopic discectomies. Further, the delivery of the disc treatment device may be conducted under endoscopic or other similar visualization techniques.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. In addition, all references cited herein are indicative of the level of skill in the art and are hereby incorporated by reference in their entirety.

What is claimed is:

1. A method of preventing effluence from a disc cavity of a damaged intervertebral disc having an annulus Fibrosus having an opening, said method comprising inserting a fibrous plug into the cavity of said disc defined by the annulus fibrosus so as to position said fibrous plug beyond the annulus fibrosus and completely within the cavity, with said fibrous plug abutting an inner surface of the annulus fibrosus so as to block effluence from said opening.

2. The method of claim 1, wherein said fibrous plug is comprised of fibers coated with a solid carrier matrix comprising the tissue growth factor.

3. The method of claim 1, wherein said plug is cylindrical.

4. The method of claim 1, wherein said fibrous plug comprises synthetic fibers.

5. The method of claim 4, wherein said synthetic fibers comprise a material selected from the group consisting of polyamides, polyesters, polyethylenes, polyacrylonitriles, polyurethanes, polypropylenes and mixtures thereof.

6. The method of claim 1, wherein said fibrous plug comprises natural fibers.

7. The method of claim 6, wherein said natural fibers comprise collagen.

8. The method of claim 6, wherein said natural fibers comprise elastin.

9. The method of claim 1, wherein said plug comprises an effective amount of a tissue growth composition to stimulate disc repair.

10. The method of claim 9, wherein said tissue growth composition is incorporated within said body.

11. The method of claim 9, wherein said tissue growth composition is bound to an exterior surface of said body.

12. The method of claim 11, wherein said tissue growth composition comprises a biocompatible polymeric carrier.

13. The method of claim 12, wherein said polymer is a naturally occurring polymer.

14. The method of claim 13, wherein said polymer is collagen.

15. The method of claim 9, wherein said tissue growth composition comprises tissue growth factor selected from the group consisting of Transforming Growth Factor-beta (TGF-B) and members of the TGF-B superfamily, Fibroblast Growth Factor (FGF) and members of the FGF family, Platelet Derived Growth Factor (PDGF) and members of the PDGF family, members of the hedgehog family of proteins, interleukins (IIs), Insulin-like Growth Factor (IGF) and members of the IGF family, colony-stimulating factor (CSF) and members of the CSF family, Growth Differentiation Factors (GDFs), Cartilage Derived Growth Factors (CDGFs), Cartilage Derived Morphogenic Proteins (CDMPs), Bone Morphogenetic Proteins (BMPs), and mixtures thereof.

16. The method of claim 15, wherein said tissue growth factor is a recombinant human protein.

17. The method of claim 15, wherein said tissue growth factor is a bone morphogenic protein.

18. The method of claim 17, wherein said bone morphogenetic protein is selected from the group consisting of BMP-1, BMP-2, BMP-3, BMP-4, BMP-5, BMP-6, BMP-7, BMP-8, BMP-9, BMP-10, BMP-11, BMP-12, BMP-13, BMP-14, BMP-15, BMP-16, BMP-17, BMP-18, and mixtures or heterodimers thereof.

19. A method for treating a damaged intervertebral disc, comprising:
(a) providing an opening in an annulus fibrosus of the damaged intervertebral disc;
(b) passing a non-prosthetic delivery body through and beyond said opening and completely into a disc cavity defined by the annulus fibrosus, the delivery body incorporating a tissue growth factor; and
(c) the delivery body releasing the tissue growth factor in the disc cavity and promoting tissue growth in the disc cavity.

20. The method of claim 19, wherein said delivery body comprises a natural polymer.

21. The method of claim 19, wherein said delivery body is cylindrical.

22. The method of claim 19, wherein said delivery body comprises synthetic fibers.

23. The method of claim 22, wherein said synthetic fibers comprise a material selected from the group consisting of polyamides, polyesters, polyethylenes, polyacrylonitriles, polyurethanes, polypropylenes and mixtures thereof.

24. The method of claim 19, wherein said delivery body comprises natural fibers.

25. The method of claim 24, wherein said natural fibers comprise collagen.

26. The method of claim 24, wherein said natural fibers comprise elastin.

27. The method of claim 19, wherein said tissue growth factor is selected from the group consisting of Transforming Growth Factor-beta (TGF-B) and members of the TGF-B superfamily, Fibroblast Growth Factor (FGF) and members of the FGF family, Platelet Derived Growth Factor (PDGF) and members of the PDGF family, members of the hedgehog family of proteins, interleukins (Us), Insulin-like Growth Factor (IGF) and members of the IGF family, colony-stimulating factor (CSF) and members of the CSF family, Growth Differentiation Factors (GDFs), Cartilage Derived Growth Factors (CDGFs), Cartilage Derived Morphogenic Proteins (CDMPs), Bone Morphogenetic Proteins (BMPs), and mixtures thereof.

28. The method of claim 27, wherein said tissue growth factor is a recombinant human protein.

29. The method of claim 27, wherein said tissue growth factor is a bone morphogenic protein.

30. The method of claim 29, wherein said bone morphogenetic protein is selected from the group consisting of BMP-1, BMP-2, BMP-3, BMP-4, BMP-5, BMP-6, BMP-7, BMP-8, BMP-9, BMP-10, BMP-11, BMP-12, BMP-13, BMP-14, BMP-15, BMP-16, BMP-17, BMP-18, and mixtures or heterodimers thereof.

31. The method of claim 19, wherein said delivery body incorporates a composition comprising the tissue growth factor within a biocompatible carrier.

32. The method of claim 31, wherein said composition is incorporated within said delivery body.

33. The method of claim 31, wherein said composition is bound to an exterior surface of said delivery body.

34. The method of claim 31, wherein said biocompatible carrier comprises a polymer.

35. The method of claim 34, wherein said polymer is a naturally occurring polymer.

36. The method of claim 35, wherein said polymer is collagen.

37. A method for treating a damaged intervertebral disc in a vertebrate, the intervertebral disc having an annulus fibrosus having a rupture opening, the method comprising introducing at least a first amount of a tissue growth factor into a disc cavity of the ruptured intervertebral disc, and sealing the rupture opening of the annulus with a sealant device, wherein said first amount of tissue growth factor is separate from said sealant device during said introducing step, and wherein said introducing step is conducted before or after said sealing step.

38. The method of claim 37, wherein said sealant device comprises synthetic fibers.

39. The method of claim 37, wherein said sealant device comprises a natural polymer.

40. The method of claim 37, wherein said sealant device incorporates a second amount of a tissue growth factor.

41. The method of claim 37, wherein said sealant device has a second amount of a tissue growth factor bound to an exterior surface of said sealant device.

42. The method of claim 37, wherein said sealant device comprises natural fibers.

43. The method of claim 42, wherein said natural fibers comprise collagen.

44. The method of claim 42, wherein said natural fibers comprise elastin.

45. The method of claim 37, wherein said tissue growth factor is incorporated within a biocompatible carrier.

46. The method of claim 45, wherein said biocompatible carrier comprises a naturally occurring polymer.

47. The method of claim 46, wherein said polymer is collagen.

48. The method of claim 37, wherein said tissue growth factor is selected from the group consisting of Transforming Growth Factor-beta (TGF-B) and members of the TGF-B superfamily, Fibroblast Growth Factor (FGF) and members of the FGF family, Platelet Derived Growth Factor (PDGF) and members of the PDGF family, members of the hedgehog family of proteins, interleukins (IIs), Insulin-like Growth Factor (IGF) and members of the IGF family, colony-stimulating factor (CSF) and members of the CSF family, Growth Differentiation Factors (GDFs), Cartilage Derived Growth Factors (CDGFs), Cartilage Derived Morphogenic Proteins (CDMPs), Bone Morphogenetic Proteins (BMPs), and mixtures thereof.

49. The method of claim 48, wherein said tissue growth factor is a bone morphogenic protein.

50. The method of claim 49, wherein said bone morphogenetic protein is selected from the group consisting of BMP-1, BMP-2, BMP-3, BMP-4, BMP-5, BMP-6, BMP-7, BMP-8, BMP-9, BMP-10, BMP-11, BMP-12, BMP-13, BMP-14, BMP-15, BMP-16, BMP-17, BMP-18, and mixtures or heterodimers thereof.

* * * * *